United States Patent [19]

Kullas et al.

[11] Patent Number: 4,723,547
[45] Date of Patent: Feb. 9, 1988

[54] ANTI-OBESITY BALLOON PLACEMENT SYSTEM

[75] Inventors: Karen E. Kullas, Taunton, Mass.; Joseph Giusto, Warren, R.I.

[73] Assignee: C. R. Bard, Inc., Murray Hill, N.J.

[21] Appl. No.: 731,673

[22] Filed: May 7, 1985

[51] Int. Cl.$^4$ ............................................. A61B 17/34
[52] U.S. Cl. .................................. 128/329 R; 128/344
[58] Field of Search ............... 128/1 R, 303 R, 329 R, 128/325, 344

[56] References Cited

U.S. PATENT DOCUMENTS

| | | | |
|---|---|---|---|
| 2,493,326 | 1/1950 | Trinder | 128/344 |
| 3,882,854 | 5/1975 | Hulka et al. | 128/325 X |
| 4,133,315 | 1/1979 | Berman et al. | 128/344 X |
| 4,271,839 | 6/1981 | Fogarty et al. | 128/344 |
| 4,315,509 | 2/1982 | Smit | 128/303 R |
| 4,416,267 | 11/1983 | Garren et al. | 128/344 X |
| 4,485,805 | 12/1984 | Foster, Jr. | 128/344 X |
| 4,517,979 | 5/1985 | Pacenka | 128/344 X |

Primary Examiner—Steven E. Warner
Attorney, Agent, or Firm—Wolf, Greenfield & Sacks

[57] ABSTRACT

An anti-obesity balloon and a placement system for the balloon includes a balloon with a needle-pierceable, self-sealing plug and an insertion catheter having a needle at its distal end. The needle is movable between an extended position in which it protrudes distally of the insertion catheter and a retracted position in which it is withdrawn interiorly of the insertion catheter. A handle arrangement is provided at the proximal end of the insertion catheter to control the position of the needle. Means are provided for aspirating and inflating the balloon. The balloon structure and insertion catheter structure protect and enclosed the sharp tip of the needle at all times during insertion and withdrawal of the insertion catheter. The insertion catheter is detachable from the balloon, after the balloon has been inflated in the patient's stomach, in a manner which imposes no force or load on the balloon.

14 Claims, 15 Drawing Figures

ANTI-OBESITY BALLOON PLACEMENT SYSTEM

FIELD OF THE INVENTION

This invention relates to techniques for treating obesity by placement of a balloon in the patient's stomach to reduce the patient's appetite and control the patient's food intake.

BACKGROUND OF THE INVENTION

Various techniques and devices have been proposed and used to treat obese patients so as to reduce their weight and to maintain their weight at a reduced, more acceptable level. The techniques have included surgical as well as non-surgical approaches. By way of example, one such surgical procedure involves an abdominal surgical procedure in which the stomach is surgically exposed and then is stapled in a manner to reduce the available volume of the stomach. In another surgical technique the stomach is wrapped in a non-expandable fabric or mesh so that it cannot expand beyond the volume defined by the wrap. Other surgical procedures for the treatment of obesity include shortening or placing shunts in the intestinal tract so as to reduce the time during which food is exposed to the patient's digestive process.

Also among the techniques which have been proposed has been to place a balloon within a patient's stomach so as to occupy a substantial volume of the stomach thereby to limit the available unfilled volume within the stomach and to provide the patient with an early sensation of satiety. The balloon systems which have been proposed have suffered from various difficulties and none is believed to have achieved any practical lasting use. Among the difficulties have been in the valving arrangement for inflating the balloon and for maintaining the balloon in an inflated condition over an extended period of time. Additionally, the balloon structures and placement techniques which have been proposed generally have been cumbersome and awkward. It is among the general objects of the present invention to provide an improved anti-obesity balloon and placement system which avoids the difficulties presented by the prior proposed devices.

SUMMARY OF THE INVENTION

The system includes a balloon formed from neoprene latex. The balloon has an internally everted neck in which a thick natural rubber plug is secured. The plug is receptive to a needle at the distal end of the placement device and is self-sealing when the needle is withdrawn. In order to insert the device into the patient the balloon is attached to the distal end of an insertion catheter arrangement which has the needle at its distal end. The needle is inserted into and through the plug to communicate with the interior of the balloon. The balloon is collapsed by aspiration with a syringe attached to the proximal end of the catheter arrangement which is in communication with the needle. The catheter, with the collapsed balloon attached then is inserted orally through the patient's esophagus and into his stomach. Once the balloon is in the stomach, the syringe is operated to inflate the balloon. The needle then is withdrawn from the balloon plug which self-seals and the insertion catheter device is removed from the patient. The entire procedure can be completed in a few minutes and requires no surgery.

In one aspect of the invention the system protects and covers the needle at all times so that the needle cannot inadvertently damage the balloon or injure the patient. The catheter arrangement for inserting the balloon includes a system in which the needle is retractable into the distal end of the insertion catheter simultaneously as the needle is withdrawn from the balloon plug valve. When the insertion catheter is withdrawn from the patient the needle will have been retracted and enclosed within the distal end of the catheter. When the balloon is attached to the needle for insertion into the patient, puncture of the balloon is avoided by the special internal shape of the balloon plug. The plug is provided with an internal hood which surrounds the distal tip of the needle to prevent it from contacting the balloon itself while permitting exposure of the lumen of the needle to the interior volume of the balloon.

The insertion catheter system includes an outer guide sheath and an inner inflation tube which is slidable in the sheath. The needle is attached to the distal end of the inner tube. A handle at the proximal end of the insertion catheter is connected to each of the inner tube and outer sheath and can be manipulated between two positions, including an extended position in which the inner tube and needle project distally beyond the distal end of the sheath, and a retracted position in which the inner tube is withdrawn proximally to withdraw the needle within the distal tip of the sheath. The handle also includes locking means to secure the handle in either of the two positions. That serves to provide a definite indication that the needle is in its fully extended or fully retracted position. The handle also includes a fitting which is in communication with the lumen of the inner tube and by which a syringe can be connected for inflation and deflation of the balloon.

Another aspect of the invention relates to the manner in which the insertion catheter detaches from the balloon. When inserted, the balloon is attached to the needle at the distal end of the catheter. The catheter then is in an extended configuration in which the needle projects distally beyond the distal tip of the outer sheath. When the handle is operated to retract the inner tube and withdraw the needle from the plug, the distal tip of the outer sheath bears against the outwardly facing surface of the balloon plug to provide a bearing support during retraction. The entire force of detachment of the needle from the balloon plug is taken up by the balloon plug, with none of the force being applied to the balloon.

It is among the general objects of the invention to provide an improved obesity balloon and placement system therefor.

Another object of the invention is to provide an obesity balloon and placement system which is easy to use.

Another object of the invention is to provide an anti-obesity balloon and placement system in which the entire balloon placement procedure may be completed within several minutes.

A further object of the invention is to provide an obesity balloon placement system which is inexpensive and may be disposed of after a single use.

Another object of the invention is to provide an anti-obesity balloon and placement system therefore in which the risk of balloon breakage during the insertion procedure is reduced greatly.

DESCRIPTION OF THE DRAWINGS

The foregoing and other objects and advantages of the invention will be appreciated more fully from the following further description thereof, with reference to the accompanying drawings wherein.

DESCRIPTION OF THE PREFERRED EMBODIMENT

Figures 1, 3:
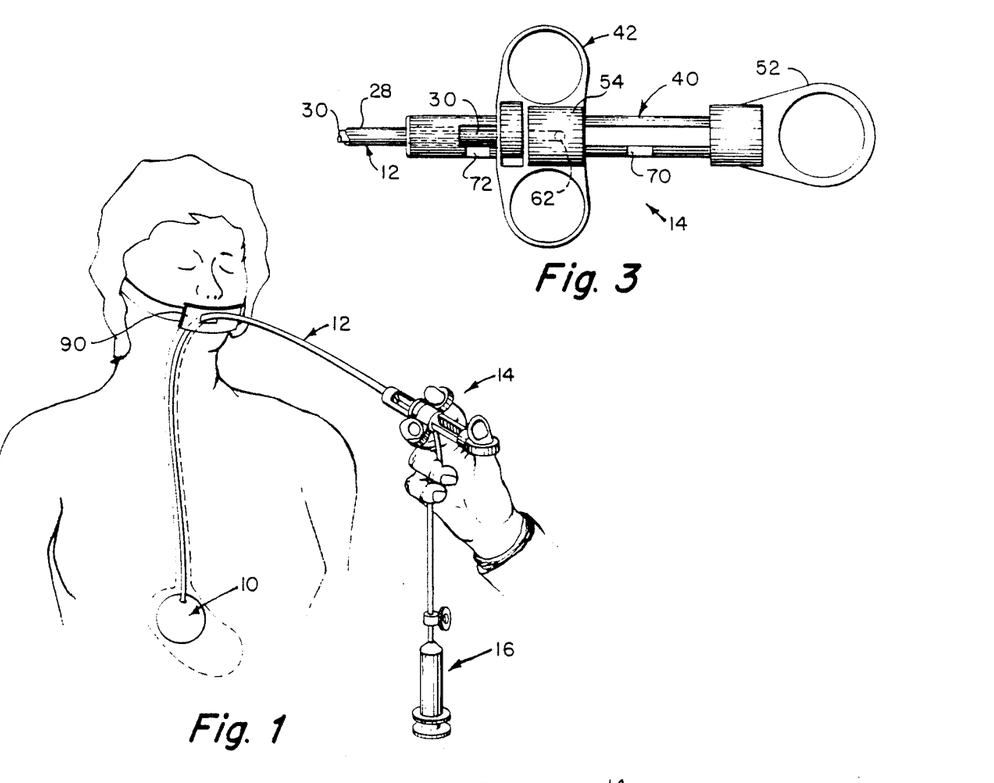
FIG. 1 is an illustration of the system in use to place the balloon in the patient's stomach.
FIG. 3 is a plan view of the handle.
Figure 2:
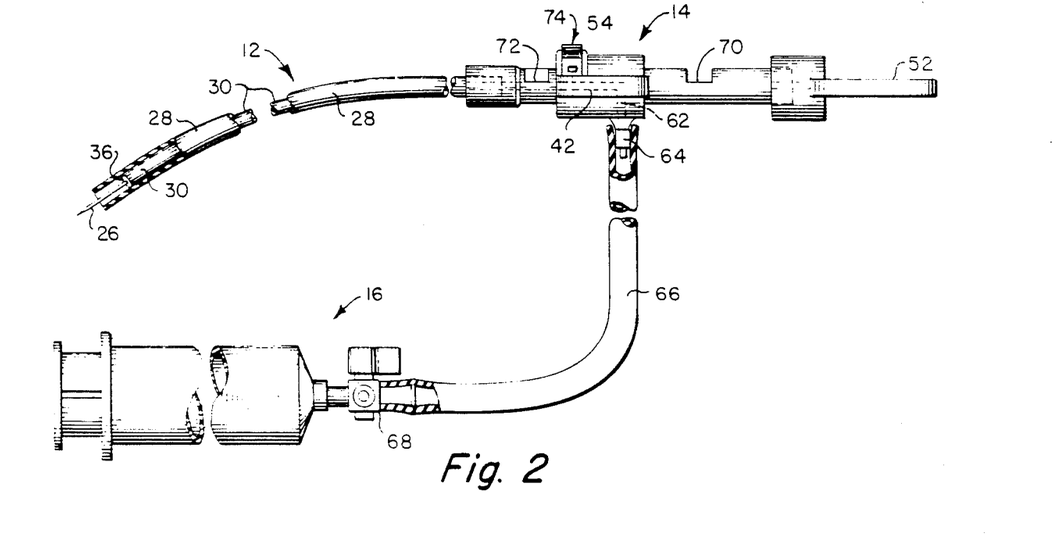
FIG. 2 is a partly fragmented, partly sectional illustration of the placement system including the insertion catheter, handle and syringe.

As shown in FIGS. 1 and 2 the system includes a balloon 10, an insertion catheter 12 having a handle 14 at its proximal end and an inflation/deflation device 16 such as a syringe.

The balloon preferably is formed, such as by dipping, from neoprene latex in a shape which will be approximately spherical when inflated. The Neoprene latex may be compounded to have radiopaque properties which facilitates placement and visualization of the balloon by fluoroscopy. The precise shape of the balloon, however, is not considered to be critical and somewhat elongated balloon shapes also are satisfactory.

Figures 10, 11, 12, 13:
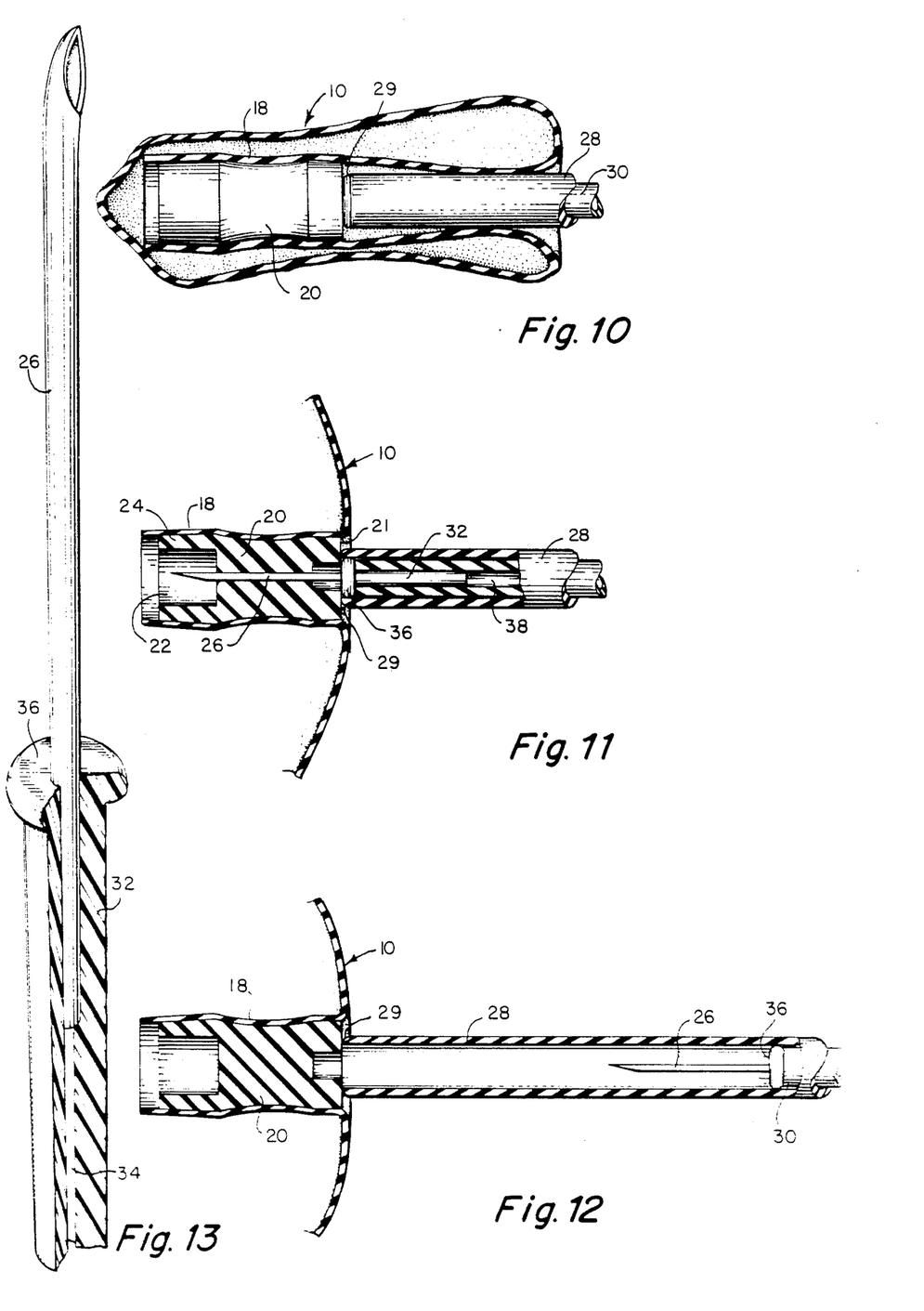
FIG. 10 is an enlarged illustration of the deflated balloon connected to the distal end of the insertion catheter.
FIG. 11 is a sectional illustration through the connected catheter and balloon plug after the balloon has been inflated but before the needle has been withdrawn.
FIG. 12 is an enlarged illustration similar to FIG. 11 showing the needle removed from the balloon plug and in a retracted position.
FIG. 13 is an enlarged illustration of the needle in its holder.

The balloon is formed with a neck 18, illustrated best in FIGS. 10-12, which is everted and extends interiorly of the balloon. An elongate thick plug 20, which is formed preferably from natural rubber, is attached adhesively within the everted neck 18. The plug 20 may have a narrowed midsection to enhance the security of the adhesive bond to the neck 18. The exposed face of the plug is substantially flush with the surface of the balloon. The inner end of the plug 20 is formed to include an axially extending socket 22. The socket is defined by a cylindrical hood 24 which extends inwardly into the balloon and is integral with the plug 20. As will be described in further detail, the plug 20 is intended to be pierced by a hollow needle 26 at the distal end of the insertion catheter 12. The parts are dimensioned relatively so that when the needle 26 is inserted into the plug 20 the distal tip of the needle will not protrude outwardly from the socket 22 and will be protected by the surrounding hood 24. Thus, when the needle 26 is inserted into the plug, the balloon 10 remains protected from the sharp tip of the needle. It may be noted that the proximal end of the plug 20 is provided with a socket 23. The socket 23 provides a convenient means by which the plug 20 can be held and mounted during attachment of the plug 20 to the balloon 10. It also may facilitate visually, the user's registration of the needle with the plug 20.

The needle should be of the non-coring type, such as the Huber type needle illustrated in FIG. 13. The needle 26 preferably is coated with a material having a low coefficient of friction, such as polytetrafluoroethylene to reduce frictional drag of the needle through the rubber. The natural rubber plug self-seals when the needle 26 is withdrawn and will not leak. The low friction coating on the needle serves a number of purposes. In addition to requiring less force to insert and withdraw the needle from the relatively thick plug, the coated needle significantly reduces the extent to which the plug is distorted, particularly when the needle is inserted. The use of an uncoated needle can present considerable difficulty because even a slight axial misalignment of an uncoated needle with the plug tends to cause the plug to bend as the needle is inserted. That increases the misalignment and can result in the needle piercing the periphery of the plug, thereby potentially exposing the sharp tip of the needle to the balloon. The use of the coated needle thus helps to maintain the axial alignment of the needle and plug when they are mated.

The insertion catheter 12 includes an elongate outer sheath 28 and an elongate inner tube 30 which is slidable longitudinally within the outer sheath 28. The needle 26 is mounted to the distal end of the inner tube 30 as shown in FIGS. 11 and 13. The needle 26 is mounted, at its proximal end, in a tubular needle holder 32. The needle holder 32 has a central passage 34 which communicates with the lumen in the needle. The distal end of the needle holder 32 is provided with an enlarged flange 36. The needle 26 is bonded in the distal end of the passage 34 and the assembly of the needle 26 and holder 32 is attached adhesively to the distal end of the inner tube 30. The needle holder 32 is received in the distal end of the lumen 38 of the tube 30 as shown in FIG. 11. The diameter of the flange 36 of needle holder 32 is substantially equal to the outer diameter of the inner tube 30.

The inner tube 30 is formed with a plurality of circumferentially spaced, longitudinally extending ribs 31 along its outer surface. The ribs serve to space the inner tube 30 from the inner surface of the sheath 28 to reduce sliding friction between the sheath 28 and inner tube 30. The ribs 31 preferably extend the full length of the inner tube 30.

The sheath preferably is formed from PVC. The inner tube 30 preferably is formed from nylon. The materials and dimensions of the inner and outer tubes should be selected so that the insertion catheter will be sufficiently flexible so that it can bend as necessary to be inserted into the patient's stomach while also being sufficiently stiff and rigid so as not to buckle under the influence of the axial force applied to the catheter during insertion. In a preferred embodiment of the invention the inner tube 30 is relatively thick-walled as compared to the wall thickness of the sheath 28. As will be described in further detail, when the inner tube 30 is in its fully extended, distal position the distal end of the outer sheath 28 and the flange 36 of the needle holder bear against the outwardly facing surface of the balloon plug 20. Thus, during insertion, the axial force is applied by both the inner tube 30 and outer sheath 28 to the plug 20. The sheath 28 and tube 30 share the load of insertion.

Figures 6A, 7:
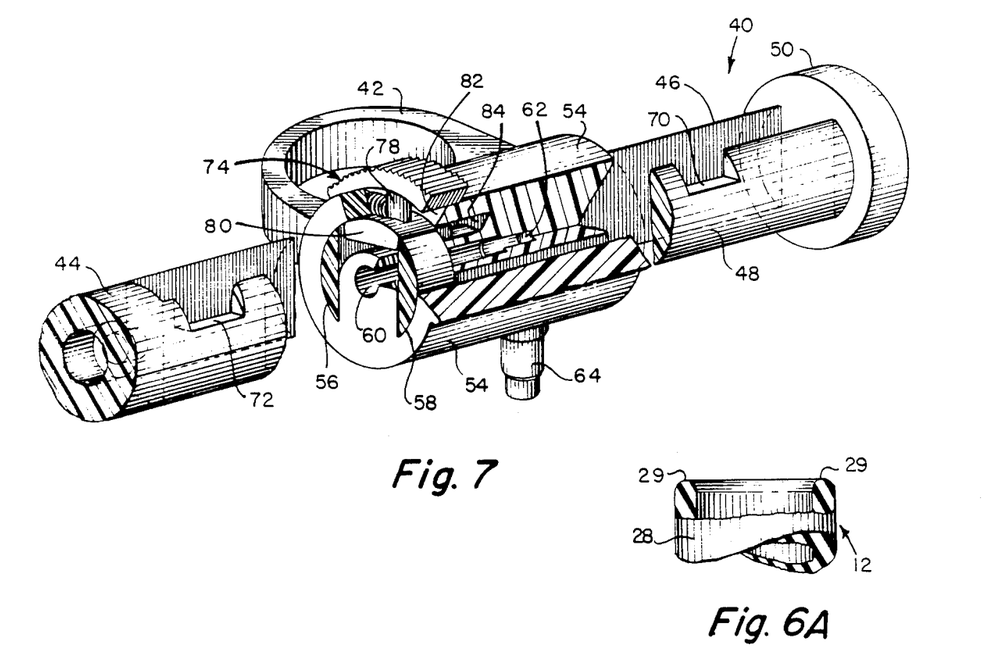
FIG. 6A is an enlarged sectional illustration of the distal tip of the sheath, as seen along the line 6A—6A of FIG. 6.
FIG. 7 is a fragmented and partly sectional illustration of the handle.

The distal tip of the sheath wall is radiused smoothly as indicated at 29 in FIG. 6A. The smoothly radiused distal tip provides for safety and comfort to minimize the chance of the distal tip causing trauma.

Figures 4, 4A, 5, 6:
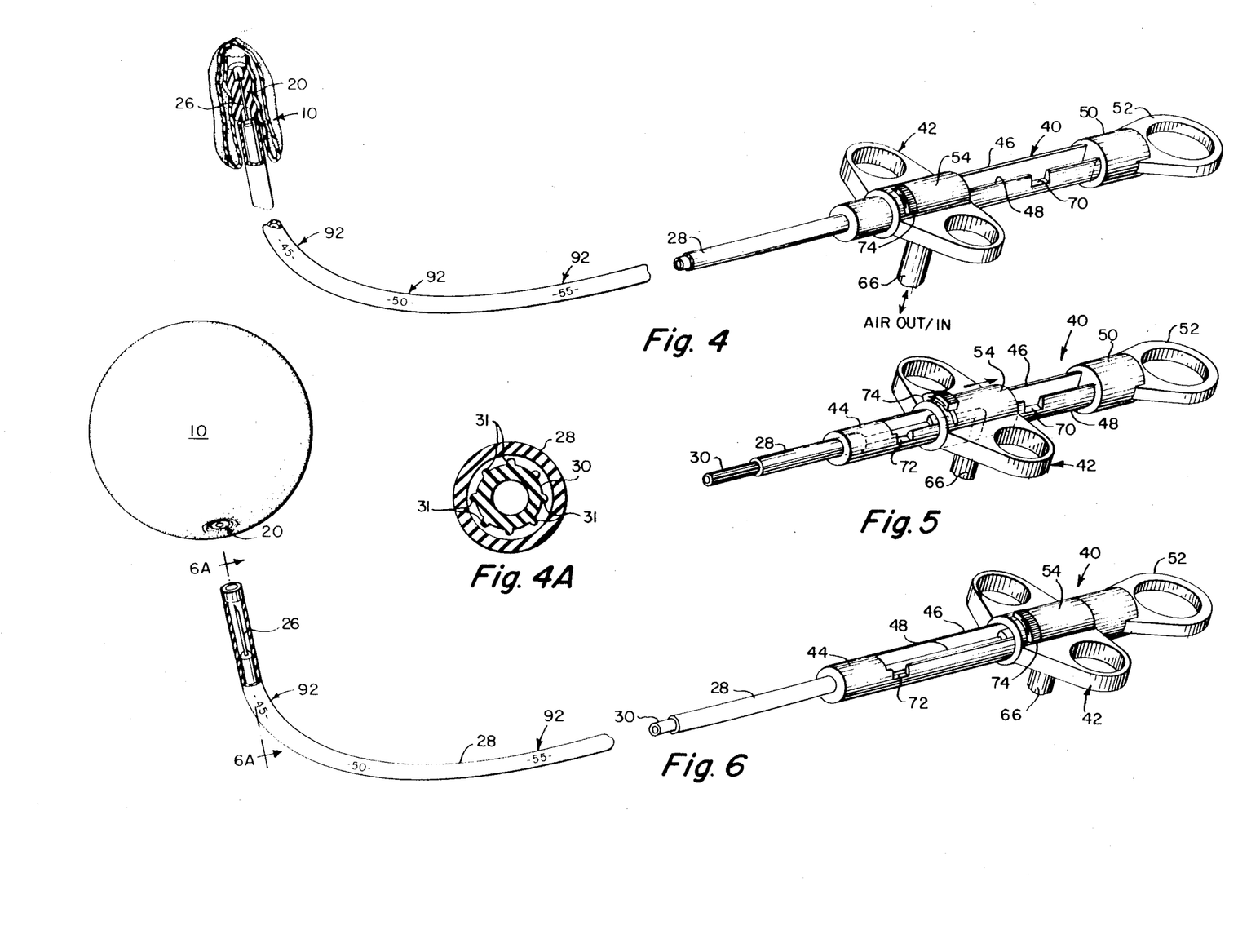
FIG. 4 is an illustration of the insertion catheter and handle with the balloon attached and in a near fully deflated condition.
FIG. 4A is a cross section as seen along the line 4A—4A of FIG. 4.
FIG. 5 is an illustration of the handle portion of the insertion system illustrating the slide as it is moved between the extended and retracted positions.
FIG. 6 is an illustration of the insertion system after the balloon has been inflated and separated and with the slide in its retracted position.

The insertion catheter 12 is connected, at its proximal end, to the handle 14. The handle 14 has a body portion 40 and a slide 42 which is movable on the body 40 between a distal position shown in FIG. 4 and a proximal position shown in FIG. 6. The outer sheath 28 is attached, at its proximal end, to the distal end of the body 40. The body 40 includes a distal portion 44 which has a socket 45 at its proximal end. The sheath 28 fits in the socket 43 and is adhesively attached thereto. The distal portion 44 of the body 40 also has a passage 45 extending from the socket 43. The passage 45 receives slidably the inner tube 30 of the insertion catheter 12. The proximal end of the inner tube 30 is connected to the slide 42. Movement of the slide 42 along the body 40 shifts the inner tube 30 within the outer sheath 28 between an extended position in which the needle 26 projects outwardly of the outer sheath 28 (FIGS. 4 and 11) and a retracted position in which the tube 30 and needle 26 are retracted into the outer sheath 30 (FIGS. 6 and 12).

The body 40 of the slide preferably is molded in a single piece from an appropriate plastic such as nylon or ABS. In the illustrative embodiment, the body 40 includes the distal portion 44 and a pair of longitudinally extending rails 46, 48. The rails 46, 48 are connected at their proximal ends by a proximal portion 50 which preferably includes a thumbhole member 52. The proximal portion is formed separately and is attached to the proximal end of the rails 46,48 after the slide has been mounted on the rails. The outer surfaces of the rails 46, 48 may be arcuate as shown and the inner facing surfaces of the rails may be flat.

The slide 42 has a central portion which, in the illustrative embodiment, is generally circular in cross section. A pair of wings with fingerholes are formed integrally with and extend outwardly from the central portion 54. The central portion 54 has a pair of longitudinally extending slots 56, 58 having a cross section corresponding to that of the rails 46, 48. The rails 46, 48 are received in the slots 56, 58 and slidably support the central portion 54. The central portion 54 includes a bore 60 at its distal end. The bore 60 receives the proximal end of the inner tube 30 which may be adhesively secured within the bore 60. An internal passageway 62 is formed in the central portion 54 and extends downwardly through a nipple 64. The nipple 64 is connectable to a tube 66 which is connected, through a three-way valve 68, to the syringe 16. Thus the syringe 16 and three-way valve 68 may be operated to pump air to or from the needle 26 by the passageway provided through the tube 66, passage 62, bore 60 and inner tube 30.

Figure 8:
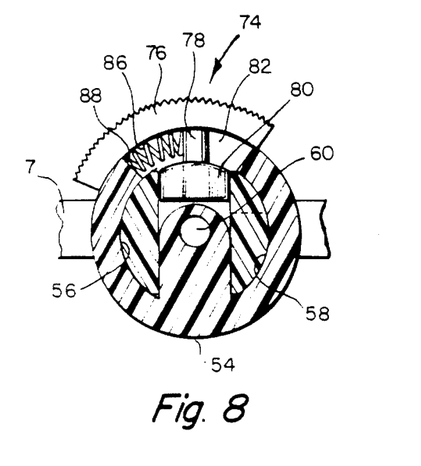
FIG. 8 is a sectional illustration taken through the handle along the line 8—8 illustrating the latch in its unlatched position.
Figure 9:
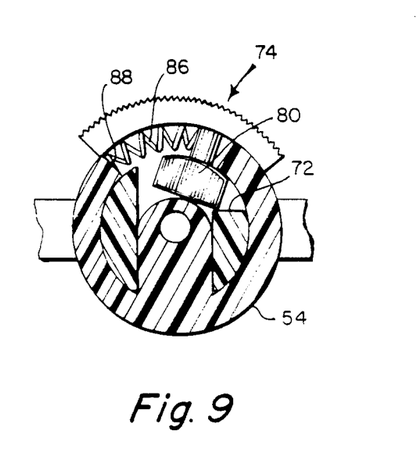
FIG. 9 is an illustration similar to FIG. 8 with the latch in its latched position.

The handle is provided with an arrangement to latch the slide in two positions, namely, a distal position corresponding to an extended needle position and a proximal position in which the needle and inner tube are retracted within the outer sheath. As shown in the drawings, and particularly in FIGS. 7-9, one of the rails 48 is provided with a pair of longitudinally spaced detent slots 70, 72 which define, respectively, the proximal and distal positions of the slide. The slide 42 carries a latch which is engagable with the detent slots 70, 72 but which can be manually released to free the slide for a movement along the rails 46, 48 to the other position. The latch, indicated generally at 74 is illustrated in FIGS. 7-9. The latch 74 is shiftable on the slide 42 circumferentially about the central portion 54 of the slide between an unlocked position shown in FIG. 8 and a locked position shown in FIG. 9. The latch 74 includes an arcuate latching slide 76 which is disposed exteriorly of the central portion 54. The latching slide 76 has an inwardly projecting pin 78 to which is secured, at its inner end, a locking tab 80. The central portion 54 is provided with arcuate slots 82, 84 to receive the pin 78 and locking tab 80, respectively, and to permit them to have limited arcuate movement between the positions illustrated in FIGS. 8 and 9. The latch 74 is biased toward the locked configuration shown in FIG. 9 by a compression spring 86 contained within the slot 82 and it can press between the pin 78 at one end and an end surface 88 at one end of the slot 82. The locking tab 80 is dimensioned with respect to the detent slots 70, 72 so that when the latch 74 is aligned with either of the detent slot 70, 72, the spring 86 will urge the latch 74 toward a locked position in which the locking tab 80 engages the detent slot. The latch 74 and detent slots are shaped so that the latch will snap abruptly and noticeably into engagement with the detent slots, preferably also making an audible click. That provides a clear, tactile and audible indication to the user that the device is secured in an extended or retracted configuration. It is preferred that the proximal detent slot 70 is located so that when the slide is latched in its proximal position the needle 26 will be withdrawn relatively deeply into the sheath 28, as suggested in FIG. 12. Additionally, when the slide is latched in its distal position it provides definite assurance that the needle is fully extended beyond the distal end of the sheath. Latching in that position also secures the needle position to facilitate pushing the balloon plug 20 onto the needle 26.

In use, the patient will have been fitted with a mouthpiece 90 as illustrated in FIG. 1. The mouthpiece may be of the type conventionally used when inserting endoscopes or gastric tubes into a patient to assure that the patient's mouth will remain open during the procedure. The balloon 10 then is attached to the distal end of the insertion catheter as indicated in FIGS. 4 and 10. Before attaching the balloon 10, the handle 14 is operated to advance the slide 42 to its distal most position to cause the tube 30 to advance and to cause the needle 26 to project distally beyond the end of the outer sheath 28. Engagement of the latch 74 with the distal detent 72 provides clear assurance that the needle 26 is extended fully and properly to its extended position. The balloon then is attached to the distal end of the catheter 12 by simply inserting the needle 26 fully into the plug 20. As described above, the plug and needle are arranged so that when the needle is inserted fully, its distal tip will be disposed within the socket 22 of the plug and will be protected by the surrounding hood 24.

After the balloon has been attached to the needle, the syringe 16 is operated to evacuate fully the balloon 10. Complete evacuation of the balloon facilitates folding up of the balloon at the distal end of the insertion catheter and facilitates insertion into the patient. It may be desirable preliminarily first to inflate the balloon as a preliminary test.

The three-way valve 68 is arranged on the syringe 16 to communicate the syringe selectively with the tube 66 or with the atmosphere. The valve 68 is operated during each stroke of the syringe. For example, when collapsing the balloon preparatory to insertion, the valve 68 connects the syringe 16 with the tube 66 during the aspiration stroke and is shifted to communicate the syringe with the atmosphere during the return stroke of the syringe. When the syringe is ready for the next aspiration stroke the valve 68 is reshifted to communicate the syringe with the tube 66.

FIGS. 4 and 10 illustrate the manner in which the balloon may be wrapped or draped about the distal end of the insertion catheter 12 during insertion. In that configuration the insertion device is inserted through the mouthpiece 90 and is advanced into the patient's stomach as indicated in FIG. 1. The position of the insertion device 12 as it is advanced into the patient may be monitored by reference to indicia 92 formed on the outer surface of the sheath 28. The indicia 92 preferably correspond to the indicia conventionally used with endoscopes and the like. Additionally, the position of the insertion device 12 and balloon 10 may be monitored fluoroscopically. The neoprene latex material from which the balloon is made has an inherently radiopaque quality which shows up well on fluoroscopy.

Once the balloon has been properly positioned in the patient's stomach, the syringe 16 and valve 68 are operated to inflate the balloon. The valve 68 is operated so that during an inflation stroke of the syringe the valve communicates the syringe 16 with the tube 66. During retraction of the syringe plunger the valve 68 is shifted to communicate with the atmosphere to draw air into the syringe. When the syringe is ready for the next inflation stroke the valve 68 is reshifted to communicate the syringe 16 with the tube 66. The extent to which the balloon is inflated is controlled by reference to the volumetric graduations of the syringe. The extent to which the balloon 10 is inflated will, of course, vary among patients and will be determined by the physician in each case.

After the balloon 10 has been inflated to its intended volume, the insertion device 12 is separated from the balloon 10. Separation is quick and simple and involves simply releasing of the latch 74 and sliding the slide 14 to its proximal position. Drawing the slide 14 to its proximal position draws the inner tube 30 together with the needle 26 proximally into the outer sheath 28. The slide 14 is drawn proximally until the latch 74 engages the proximal detent slot 70 on the body. The detent slot 70 is located so that it will not be engaged by the latch until the needle 26 has been withdrawn fully into the sheath 28. Thus, when the latch 74 engages the proximal detent slot 70, the physician is assured that the needle has been completely separated from the balloon and has been withdrawn completely into the outer sheath 28. The insertion catheter 12 then may be removed without risks to the patient, leaving the inflated balloon within the patient's stomach and completing the procedure.

The manner in which the needle 26 is withdrawn from the plug 20 is illustrated in FIG. 11. Separation is effected in a manner which imposes no load or strain on the balloon 10 and does not risk injury to the balloon such as pinching the balloon wall or pulling the plug 20 out of the neck. The sheath 28 is dimensioned with respect to the plug 20 so that when the needle 26 is retracted the distal end of the sheath 28 will bear against the outer face 21 of the plug. As the tube 30 and needle 26 are retracted, the entire resistive force is taken up by engagement of the plug 20 with the end of the sheath 28, against which the plug bears. By withdrawing the needle 26 in that manner, no load is applied to the balloon. As the needle 26 is withdrawn from the plug its sharp tip is protected and covered at all times as it is transferred from the plug to a protected position within the sheath 28. The needle, which preferably is provided with an external coating of low friction material such as PTFE, withdraws easily and quickly from the plug 20.

Thus, the invention provides a quick, effective and safe apparatus and method for placing an anti-obesity balloon in a patient's stomach. It should be understood, however that the foregoing description of the invention is intended merely to be illustrative thereof and that other modifications and embodiments may be apparent to those skilled in the art without departing from its spirit.

Having thus described the invention what we desire to claim and secure by Letters Patent is:

1. An apparatus for placing an anti-obesity balloon in a patient, the balloon having a self-sealing plug which is pierceable by a needle, the apparatus comprising:

an insertion catheter comprising an inner, elongate tube; an outer, elongate sheath; the inner tube being slidable within the sheath;

a hollow needle mounted at the distal end of the insertion catheter, the needle being attached to the distal end of the inner tube, the needle being adapted to pierce the plug;

the catheter having conduit means in communication with the needle to enable a balloon attached to the needle to be inflated and deflated;

said catheter including means for sheilding the needle to enable withdrawal of the needle without exposing the tip of the needle to the balloon or to the patient, said shielding means comprising the needle being mounted for movement between a first position in which the needle is extended out of the distal end of the insertion catheter and a second position in which the needle is withdrawn into the distal end of the insertion catheter and means for effecting said movement of the needle between said first and second positions;

said inner tube and outer sheath being relatively movable between positions in which said needle is in said first and said second positions;

handle means at the proximal end of the insertion catheter, the handle means being connected to each of the sheath and the tube, the handle means being constructed and arranged to effect said relative movement between the inner tube and outer sheath;

said handle means having two lockable positions corresponding, respectively, to said first position and said second position of the needle.

2. An apparatus for placing an anti-obesity balloon in a patient, the balloon having a self-sealing plug which is piercable by a needle, the apparatus comprising:

an insertion catheter comprising an inner, elongate tube; an outer, elongate sheath; the inner tube being slidable within the sheath;

a hollow needle mounted at the distal end of the insertion catheter, the needle being attached to the distal end of the inner tube, the needle being adapted to pierce the plug;

the catheter having conduit means in communication with the needle to enable a balloon attached to the needle to be inflated and deflated;

said catheter including means for sheilding the needle to enable withdrawal of the needle without exposing the tip of the needle to the balloon or to the patient, said sheilding means comprising the needle being mounted for movement between a first position in which the needle is extended out of the distal end of the insertion catheter and a second position in which the needle is withdrawn into the distal end of the insertion catheter and means for effecting said movement of the needle between said first and second positions;

said inner tube and outer sheath being relatively movable between positions in which said needle is in said first and said second positions;

handle means at the proximal end of the insertion catheter, the handle means being connected to each of the sheath and the tube, the handle means being constructed and arranged to effect said relative movement between the inner tube and outer sheath;

a body;

a slide slidably mounted on the body;

said tube being connected to one of said body or slide;

said sheath being connected to the other of said body or slide.

3. An apparatus as defined in claim 2 wherein said tube is connected to the slide and the sheath is connected to the body of the handle.

4. An apparatus as defined in claim 3 further comprising:

said body and slide of said handle having two lockable positions corresponding to the first and second positions of the needle, said lockable positions being defined by a latch on one of said body and slide and a detent on the other of said body and said slide.

5. An apparatus as defined in claim 4 further comprising:

said detent means comprising a pair of slots formed in and spaced longitudinally along the body;

said latch means comprising a locking member and means biasing the member in a direction which, when the member is in longitudinal alignment with the slot, will bias the lock member toward and into the slot, said latch member being releasable.

6. An apparatus as defined in claim 2 further comprising means for inflating and deflating the balloon.

7. An apparatus as defined in claim 6 wherein said means for inflating and deflating the balloon comprises:

the handle having a passage formed therethrough in communication with the tube;

a conduit connected to the handle to be in communication with the passage; and means for selectivity inflating or aspirating through the conduit.

8. An apparatus as defined in claim 7 wherein said means for selectivity inflating or aspirating comprises a syringe connected to the passage through a valve means, the valve means being operable to selectively communicate the syringe with the conduit or with the atmosphere.

9. An apparatus for placing an anti-obesity balloon in a patient, the balloon having a self-sealing plug which is pierceable by a needle, the apparatus comprising:

an insertion catheter having an inner, elongate tube and an outer, elongate sheath, the inner tube being slidable within the sheath;

a hollow needle attached to the distal end of the inner tube, the needle being adapted to pierce the plug;

the catheter having a conduit means in communication with the needle to enable the balloon attached to the needle to be inflated and deflated;

said catheter including means for sheilding the needle to enable withdrawal of the needle without exposing the tip of the needle to the balloon or to the patient, said shielding means comprising the needle being mounted for movement between a first position in which the needle is extended out of the distal end of the insertion catheter and a second position in which the needle is withdrawn into the distal end of the insertion catheter and means for effecting said movement of the needle between said first and second positions;

said inner tube and outer sheath being relatively movable between positions in which said needle is in said first and said second positions;

the needle being mounted to the distal end of the tube by a needle holder, said needle holder comprising an elongate tubular member having a passage therethrough, the needle being secured to the distal end of the passage of the holder, the holder having an enlarged flange at its distal end, the proximal end of the holder being received and being secured within the distal end of the inner tube, the flange of the holder being an abutment with the distal end of the inner tube.

10. An apparatus for placing an anti-obesity balloon in a patient, the balloon having a self-sealing plug which is pierceable by a needle, the apparatus comprising:

an insertion catheter having an inner, elongate tube and an outer, elongate sheath, the inner tube being slidable within the sheath;

a hollow needle attached to the distal end of the inner tube, the needle being adapted to pierce the plug;

the catheter having a conduit means in communication with the needle to enable the balloon attached to the needle to be inflated and deflated;

said catheter including means for sheilding the needle to enable withdrawal of the needle without exposing the tip of the needle to the balloon or to the patient, said shielding means comprising the needle being mounted for movement between a first position in which the needle is extended out of the distal end of the insertion catheter and a second position in which the needle is withdrawn into the distal end of the insertion catheter and means for effecting said movement of the needle between said first and second positions;

said inner tube and outer sheath being relatively movable between positions in which said needle is in said first and said second positions;

the inner tube having a plurality of longitudinally extending ribs formed on its external surface, the ribs being engagable with the internal surface of the other sheath.

11. An anti-obesity balloon for placement in a patient's stomach comprising:
a flexible, resilent balloon resistant to gastric fluids having a neck, the neck being everted within the balloon;
a plug secured within the everted neck and not projecting outwardly of the neck, the plug being adapted to be pierced by a hollow needle and to self-seal upon withdrawal of the hollow needle, said plug being constructed to enable free fluid flow to and from the balloon;
means at the inner end of the plug for protecting the balloon from the needle when the needle projects inwardly from the plug;
the means for protecting the needle comprising the inner end of the plug being constructed to define a socket surrounded by a hood, the socket being longer than the maximum depth to which the needle is inserted through the plug whereby when the needle is inserted fully into the plug the distal tip of the needle will remain within the socket and will be surrounded by the hood.

12. An apparatus for placement of an anti-obesity balloon in a patient, the balloon having a self-sealing plug which is piercable by a needle, the apparatus comprising:
an insertion catheter;
a hollow needle mounted at the distal end of the insertion catheter, the needle being adapted to pierce the plug to communicate with the interior of the balloon;
the catheter having conduit means in communication with the needle to enable the balloon attached to the needle to be inflated and deflated;
said catheter and said plug including cooperative means for shielding the needle from the interior of the balloon while in communication with the balloon and to enable withdrawal of the needle without exposing the tip of the needle to the balloon or to the patient;
the means associated with the catheter for sheilding the needle comprising the needle being mounted for movement between a first position in which the needle is extended out of the distal end of the insertion catheter and the second position in which the needle is withdrawn into the distal end of the insertion catheter and means for effecting said movement of the needle between said first and second positions;
the insertion catheter comprising an inner, elongate tube; an outer elongate sheath; the inner tube being slidable within the sheath; the needle being attached to the distal end of the inner tube; and said inner tube and outer sheath being relatively movable between positions in which said needle is in said first and said second positions;
said anti-obesity balloon comprising a resilient, flexible balloon resistant to gastric fluid and having a neck, the neck being everted within the balloon; and a plug secured within the everted neck, the plug being adapted to be pierced by the needle and to self-seal upon withdrawl of the needle;
means at the inner end of the plug for protecting the balloon from the needle when the needle projects inwardly from the plug; and
said means for projecting the needle comprising the inner end of the plug being constructed to define a socket surrounded by a hood, the socket being longer than the maximum depth to which the needle can be inserted through the plug whereby when the needle is inserted fully into the plug the distal tip of the needle will remain within the socket and will be surrounded by the hood.

13. An anti-obesity balloon as defined in claims 11 or 12 wherein the balloon is elastic.

14. An apparatus for placing an anti-obesity balloon in a patient, the balloon having a self-sealing plug which is piercable by a needle, the apparatus comprising:
an insertion catheter;
a hollow needle mounted at the distal end of the insertion catheter, the needle being adapted to pierce the plug to communicate with the interior of the balloon;
the catheter having conduit means in communication with the needle to enable the balloon attached to the needle to be infalted and deflated;
said catheter and said plug including cooperative means for sheilding the needle from the interior of the balloon while in communication with the balloon and to enable withdrawal of the needle without exposing the tip of the needle to the balloon or to the patient;
the means associated with the plug for sheilding the needle comprising:
the plug having an inner end which is constructed to define a socket surrounded by a hood, the socket being longer than the maximum depth to which the needle can be inserted through the plug whereby when the needle is inserted fully into the plug, the distal tip of the needle will remain within the socket and will be surrounded by the hood.

* * * * *